United States Patent
Sakamoto

(10) Patent No.: US 10,004,763 B2
(45) Date of Patent: Jun. 26, 2018

(54) MAGNESIUM OXIDE GRANULES FOR PHARMACEUTICAL APPLICATIONS OR FOR USE AS FOOD ADDITIVES

(71) Applicant: KONOSHIMA CHEMICAL CO., LTD., Osaka (JP)

(72) Inventor: Kensho Sakamoto, Kagawa (JP)

(73) Assignee: KONOSHIMA CHEMICAL CO., LTD., Osaka (JP)

( * ) Notice: Subject to any disclaimer, the term of this patent is extended or adjusted under 35 U.S.C. 154(b) by 0 days. days.

(21) Appl. No.: 15/118,950

(22) PCT Filed: Feb. 25, 2014

(86) PCT No.: PCT/JP2014/054516
§ 371 (c)(1),
(2) Date: Aug. 15, 2016

(87) PCT Pub. No.: WO2015/128940
PCT Pub. Date: Sep. 3, 2015

(65) Prior Publication Data
US 2017/0042935 A1    Feb. 16, 2017

(51) Int. Cl.
*A61K 33/08* (2006.01)
*A61K 9/20* (2006.01)
*A23P 10/28* (2016.01)
*A23L 33/16* (2016.01)
*A23P 10/22* (2016.01)
*A61K 9/16* (2006.01)
*C01F 5/02* (2006.01)
*A61K 47/02* (2006.01)

(52) U.S. Cl.
CPC .............. *A61K 33/08* (2013.01); *A23L 33/16* (2016.08); *A23P 10/22* (2016.08); *A23P 10/28* (2016.08); *A61K 9/16* (2013.01); *A61K 9/1611* (2013.01); *A61K 9/20* (2013.01); *A61K 9/2095* (2013.01); *C01F 5/02* (2013.01); *A23V 2002/00* (2013.01); *A61K 47/02* (2013.01); *C01P 2006/12* (2013.01); *C01P 2006/80* (2013.01)

(58) Field of Classification Search
CPC .......... A23P 10/22; A23P 10/28; A61K 33/08; A61K 47/02; A61K 9/16; A61K 9/1611; A61K 9/20; A61K 9/2095
See application file for complete search history.

(56) References Cited

U.S. PATENT DOCUMENTS

| 4,443,425 | A  | * | 4/1984 | Sopp | ........................ | C01F 5/06 |
| | | | | | | 148/113 |
| 8,911,779 | B2 | * | 12/2014 | Kitajima | .................. | A61J 3/10 |
| | | | | | | 424/464 |
| 2012/0156293 | A1 | | 6/2012 | Kitajima et al. | | |
| 2012/0189850 | A1 | | 7/2012 | Ohsaki | | |

FOREIGN PATENT DOCUMENTS

| JP | 2001-275618 | 10/2001 |
| JP | 2003-33159 | 2/2003 |
| JP | 2003-146889 | 5/2003 |
| JP | 2006-249052 | 9/2006 |
| JP | 2009-13113 | 1/2009 |
| JP | 2009-209048 | 9/2009 |
| WO | 2011/030659 | 3/2011 |

OTHER PUBLICATIONS

International Preliminary Report on Patentability dated Aug. 30, 2016 in International Application No. PCT/JP2014/054516.
International Search Report dated May 20, 2014 in International Application No. PCT/JP2014/054516.
Office Action dated Jun. 7, 2017 in corresponding Canadian Application No. 2,938,003.
Extended European Search Report dated Sep. 21, 2017 in European Application No. 14883684.4.

* cited by examiner

*Primary Examiner* — Alexandre F Ferre
(74) *Attorney, Agent, or Firm* — Wenderoth, Lind & Ponack, L.L.P.

(57) ABSTRACT

An object of the present invention is to provide magnesium oxide that can be preferably used for pharmaceutical applications or as a food additive. In particular, the object is to provide magnesium oxide granules with which tableting problems and quality defects can be reduced, and in more particular, to provide magnesium oxide granules with which tableting problems and quality defects can be reduced and which has less heavy metal incorporation and high purity of magnesium oxide. Provided are magnesium oxide granules for pharmaceutical applications or for addition to food having a BET specific surface area of 7 to 50 m²/g and CAA80/CAA40 of 2 to 7.

15 Claims, No Drawings

MAGNESIUM OXIDE GRANULES FOR PHARMACEUTICAL APPLICATIONS OR FOR USE AS FOOD ADDITIVES

TECHNICAL FIELD

The present invention relates to magnesium oxide granules for pharmaceutical applications or for use as a food additive.

BACKGROUND ART

Magnesium oxide tablets are widely used as medical laxatives, mineral supplements, etc. (for example, Patent Literature 1 to 3).

Generally, tablets are manufactured by compression molding of raw materials. This step of compression molding is called tableting step. In a tableting step, compression action is continuously repeated at high speed. Under such conditions, stress and/or density distribution occurs in the tablets, resulting in heterogeneous inner structure. The heterogeneity is considered to be the primary cause of tableting problems and quality defects, etc.

Examples of the tableting problems include capping, laminating, sticking, picking, etc. Capping is a phenomenon in which the top of a tablet separates from the rest and comes off like a cap, which occurs after the molding, during or after the ejection of the tablet from the die. Laminating is a defect even worse than capping and is a phenomenon in which a tablet (not the top but the intermediate part) separates into horizontal layers. Sticking is a phenomenon in which powder adheres to the punch (compression rod) during the compression step and cause cavity-like defects on the surface of a tablet. Chipping is a phenomenon in which the surface of a tablet is slightly damaged for a similar reason. These tableting problems are chiefly attributable to the characteristics of the raw materials.

Examples of the quality defects include tablet defects including cracking, chipping, or dust fall that occurs even in usual usage conditions. Such quality defects mainly result from insufficient strength (hardness) of the tablets.

Also in the production of magnesium oxide tablets, in particular when magnesium oxide of high purity is used as a raw material, there arise the above tableting problems and quality defects.

Magnesium oxide is produced by the calcination of magnesium carbonate or is produced by the addition of calcium hydroxide to sea water or an aqueous solution of magnesium chloride (bittern or salt water) to give magnesium hydroxide, followed by filtration, drying, and calcination (Patent Literature 4).

The above-mentioned magnesium oxide produced by the calcination of magnesium hydroxide has varied characteristics depending on the calcination temperature, and is used for different applications. For example, magnesium oxide produced by calcination of magnesium hydroxide at high temperature of 1500° C. or higher has little activity and has high-temperature resistance and fire resistance. Such magnesium oxide is used as a refractory material, that is, as a raw material for basic refractory bricks, unshaped refractory, etc. Magnesium oxide obtainable by calcination of magnesium hydroxide at 450 to 1300° C. has relatively high activity, and is used as a raw material for magnesia cement, as an additive (mineral source) for fertilizers and foodstuffs, as a raw material for medicinal products, such as an antacid and a laxative, etc. This type of magnesium oxide is, when used as an additive for fertilizers and foodstuffs or as a raw material for medicinal products, directly or indirectly taken into the human body; or when used as a raw material for cosmetics, brought into contact with the human body. Therefore, magnesium oxide having less heavy metal incorporation (less heavy metal content) and having high purity is desired.

As described above, there has been a desire for the development of magnesium oxide that can be preferably used for pharmaceutical applications or as a food additive, has high purity, and can be tableted with reduced problems.

CITATION LIST

Patent Literature

Patent Literature 1: JP 2003-146889 A
Patent Literature 2: WO 2011/030659
Patent Literature 3: JP 2009-13113 A
Patent Literature 4: JP 2001-275618 A

SUMMARY OF INVENTION

Technical Problem

In view of the above circumstances, a main object of the present invention is to provide magnesium oxide that can be preferably used for pharmaceutical applications or as a food additive. In particular, the object is to provide magnesium oxide granules with which tableting problems and quality defects can be reduced, and in more particular, to provide magnesium oxide granules with which tableting problems and quality defects can be reduced and which has less heavy metal incorporation and high purity of magnesium oxide.

Solution to Problem

To achieve the object described above, the present inventor has wholeheartedly carried out investigations, and obtained the following finding. Use of magnesium oxide granules having a BET specific surface area of about 7 to 50 $m^2/g$ and an activity level (described later) within a predetermined range surprisingly gives tablets with an improved tablet strength and reduces tableting problems in the production of magnesium oxide tablets, which is a significant and excellent effect specific to the present invention. Based on the finding, the present inventor conducted further research and completed the present invention.

That is, the present invention relates to the following.
(1) Magnesium oxide granules for pharmaceutical applications or for addition to food having a BET specific surface area of 7 to 50 $m^2/g$ and CAA80/CAA40 of 2 to 7.
(2) The magnesium oxide granules according to the above (1) having a BET specific surface area of 10 to 45 $m^2/g$ and CAA80/CAA40 of 2.2 to 6.
(3) The magnesium oxide granules according to the above (1) or (2) having a bulk density of 700 to 1000 g/L.
(4) The magnesium oxide granules according to any one of the above (1) to (3) having a magnesium oxide purity (assay) of 96% or higher.
(5) The magnesium oxide granules according to any one of the above (1) to (4), wherein granules having a particle diameter of less than 150 μm account for 10% by weight or less of the total weight of the magnesium oxide granules.
(6) The magnesium oxide granules according to any one of the above (1) to (5) containing 20 ppm by weight or less of Pb and 4 ppm by weight or less of As relative to the total weight of the magnesium oxide granules.

(7) A method for producing the magnesium oxide granules according to any one of the above (1) to (6), comprising the steps of mixing a medium-active magnesium oxide and a low-active magnesium oxide at a weight ratio of 10:90 to 80:20, applying pressure to the mixture, and grinding the mixture.

(8) A method for producing a magnesium oxide tablet, comprising tableting the magnesium oxide granules according to anyone of the above (1) to (6).

(9) A magnesium oxide tablet containing the magnesium oxide granules according to any one of the above (1) to (6).

Advantageous Effects of Invention

With the use of the magnesium oxide granules of the present invention, tableting problems in the production of magnesium oxide tablets can be reduced, and quality defects resulting from insufficient strength of the tablets can also be reduced. In addition, since the magnesium oxide granules of the present invention have less heavy metal content and high purity of magnesium oxide, the present invention can provide safe magnesium oxide granules that can be preferably used for pharmaceutical applications or as a food additive.

DESCRIPTION OF EMBODIMENTS

An aspect of the present invention relates to magnesium oxide granules for pharmaceutical applications or for use as a food additive. By using the magnesium oxide granules of the present invention, tableting problems in the production of tablets and/or the strength of the resulting tablets can preferably be improved.

First, the physical properties of the magnesium oxide granules of the present invention will be described.

Herein, magnesium oxide may be represented as "MgO".

The BET specific surface area of the magnesium oxide granules of the present invention is usually about 7 to about 50 $m^2/g$. In terms of the improvement in tableting problems in the production of tablets or the improvement in the tablet strength, the BET specific surface area is preferably about 10 to about 45 $m^2/g$, and more preferably about 12 to about 40 $m^2/g$.

The CAA80/CAA40 of the magnesium oxide granules of the present invention is usually about 2 to about 7. In terms of the improvement in tableting problems in the production of tablets and/or the improvement in the tablet strength, the CAA80/CAA40 is preferably about 2.2 to about 6, and more preferably about 2.4 to about 5.

In the present invention, "CAA" is an index that indicates the activity level of a magnesium oxide, and is the time required for a predetermined amount of magnesium oxide to react with citric acid. CAA80 is the time after the addition of the predetermined amount of magnesium oxide to citric acid until 80 mol % of the total amount of magnesium oxide has reacted with the citric acid. Similarly, CAA40 is the time after the addition of the predetermined amount of magnesium oxide to citric acid until 40 mol % of the total amount of magnesium oxide has reacted with the citric acid. For a specific measuring method, reference may be made to the Examples described later.

"CAA80/CAA40" means the ratio of CAA80 to CAA40.

Regarding CAA, JP 07-187662 A describes that the activity of a magnesium oxide was measured in a similar manner as above.

In an embodiment of the present invention, the BET specific surface area of the magnesium oxide granules is about 7 to about 50 $m^2/g$, and the CAA80/CAA40 thereof is about 2 to about 7. In terms of the improvement in tableting problems in the production of tablets and/or the improvement in the tablet strength, preferably the BET specific surface area is about 10 to about 45 $m^2/g$ and the CAA80/CAA40 is about 2.2 to about 6, and more preferably the BET specific surface area is about 12 to about 40 $m^2/g$ and the CAA80/CAA40 is about 2.4 to about 5.

In another embodiment of the present invention, the bulk density of the magnesium oxide granules is not particularly limited as long as improvement is achieved in the tableting problems or in the tablet strength, but preferably is about 700 to about 1000 g/L, and more preferably about 750 to about 990 g/L.

In the present invention, the "bulk density" is the bulk density defined in the Japanese pharmacopoeia.

In a preferred embodiment of the present invention, the BET specific surface area of the magnesium oxide granules is about 7 to about 50 $m^2/g$, the CAA80/CAA40 thereof is about 2 to about 7, and the bulk density thereof is about 700 to about 1000 g/L.

Further, in an embodiment of the present invention, the particle diameter of the magnesium oxide granules is not particularly limited as long as improvement is achieved in the tableting problems or in the tablet strength, but the percentage of granules having a particle diameter of less than about 150 μm is usually about 10% by weight or less, preferably about 9% by weight or less, and more preferably about 8% by weight or less relative to the total weight of the granules.

The average particle diameter of the magnesium oxide granules is not particularly limited, and is, for example, usually about 150 to about 425 μm. In terms of the improvement in tableting problems or the improvement in the tablet strength, the average particle diameter is preferably about 180 to about 400 μm, and more preferably about 200 to about 380 μm. The method for measuring the particle diameter of the magnesium oxide granules may be any method that is usually used in the art. Regardless of the measuring method, when the obtained value is within the above ranges, the magnesium oxide granules are within the technical scope of the present invention.

In another embodiment of the present invention, the purity (assay) of the magnesium oxide granules is, in view of its use for pharmaceutical applications or use as a food additive, preferably about 96% or higher, more preferably about 96.5% or higher, and still more preferably 97% or higher.

In the present invention, the purity (assay) of the magnesium oxide granules is a value determined in accordance with the United States Pharmacopeia (USP). Specifically, calcination is performed at 800° C. until the resulting magnesium oxide reaches constant mass; 0.5 g of the magnesium oxide is weighed out and 30 mL of 1 N sulfuric acid is added thereto for dissolution; and the solution is titrated with 1 N sodium hydroxide for calculation of the purity.

In a preferred embodiment of the present invention, the lead (Pb) content is about 20 ppm or less and the arsenic (As) content is about 4 ppm or less, and more preferably the Pb content is about 10 ppm or less and the As content is about 3 ppm or less, relative to the total weight of the magnesium oxide granules. Such magnesium oxide granules can be safely used for pharmaceutical applications or as a food additive.

Next, the production method of the magnesium oxide granules of the present invention will be described.

The magnesium oxide used for the production of the magnesium oxide granules of the present invention may be produced by a publicly known method, a conventional method, or a method equivalent thereto.

In an embodiment of the present invention, the magnesium oxide is produced by calcination of magnesium hydroxide. The production method of magnesium hydroxide used in the present invention has already been fully established in the art, and therefore, the present invention may be implemented in accordance with the production method. The magnesium hydroxide used may also be a commercial product.

In an embodiment of the present invention, when the magnesium oxide is produced by calcination of the magnesium hydroxide, it is preferable that magnesium oxides having different activity levels from each other are produced by calcining the magnesium hydroxide at different temperatures.

Herein, a magnesium oxide obtainable by calcination of magnesium hydroxide at a calcination temperature of about 1000 to about 2000° C. is called "low-active magnesium oxide", and a magnesium oxide obtainable by calcination at a calcination temperature of about 450 to about 900° C. is called "medium-active magnesium oxide". The calcination time is not particularly limited, and for example, is usually about 30 minutes to about 5 hours, and preferably about 1 hour to about 3 hours.

The low-active magnesium oxide preferably has a BET specific surface area of about 0.05 to about 15 $m^2/g$, and more preferably about 0.1 to about 10 $m^2/g$. Also, the low-active magnesium oxide preferably has CAA80 of about 550 to about 850 seconds, more preferably about 600 to about 800 seconds, and preferably has CAA40 of about 250 to about 550 seconds, more preferably about 300 to about 500 seconds.

The medium-active magnesium oxide preferably has a BET specific surface area of about 20 to about 80 $m^2/g$, and more preferably about 25 to about 75 $m^2/g$. Also, the medium-active magnesium oxide preferably has CAA80 of about 100 to about 300 seconds, more preferably about 100 to about 250 seconds, and preferably has CAA40 of about 50 to about 100 seconds, more preferably about 60 to about 95 seconds.

In the present invention, the method for measuring the BET specific surface area may be any method that is usually used in the art and is not particularly limited. Regardless of the measuring method, when the obtained value is within the above ranges, the magnesium oxide granules are within the technical scope of the present invention. Specific examples of the method for measuring the BET specific surface area include a method in which a test sample (magnesium oxide granules) is subjected to pretreatment with heat under nitrogen gas atmosphere and then measured by the nitrogen gas adsorption method using a BET specific surface area measuring apparatus. The pretreatment may be performed, for example, under nitrogen gas atmosphere at about 130° C. for about 30 minutes. The apparatus used for the pretreatment and the apparatus used for measuring the BET specific surface area are not particularly limited, and may be any apparatuses that usually used in the art.

In a preferred embodiment of the present invention, the magnesium oxide granules are preferably produced by mixing the low-active magnesium oxide with the medium-active magnesium oxide, applying pressure to the mixture, and subsequently grinding the mixture. In this embodiment, the mixing ratio of the low-active magnesium oxide and the medium-active magnesium oxide is not particularly limited, but in view of obtaining magnesium oxide granules having desired physical properties, it is usually preferable that the wt. % ratio of the medium-active magnesium oxide:the low-active magnesium oxide is within the range of 10:90 to 80:20. The mixing ratio may be selected as appropriate to obtain magnesium oxide granules having desired physical properties. Increasing the ratio of the low-active magnesium oxide increases the bulk density and the purity but decreases the BET specific surface area and the tablet strength.

In the production of the magnesium oxide granules, the conditions at the time when pressure is applied to the mixture of the low-active magnesium oxide and the medium-active magnesium oxide are not particularly limited. The pressure is usually about 5 to about 35 MPa, and in view of obtaining magnesium oxide granules having desired physical properties, is preferably about 8 to about 30 MPa, more preferably about 10 to about 25 MPa. The apparatus used for the pressurization is not particularly limited, and a roller compactor or the like may be used, for example.

The method for the grinding after the pressurization is not particularly limited, and the grinding may be performed using, for example, a granulator. The granulator is not particularly limited, and examples thereof include a roll granulator. Specifically, the grinding may be performed by a method in which a roll granulator having vertically arranged three sets of rollers is used. The rollers are rotated, and pressurized magnesium oxide is passed through the clearance between the rollers of each set.

Magnesium oxide tablets containing the magnesium oxide granules are also included in the scope of the present invention. The method for producing tablets has already been fully established, and therefore the tablet production in the present invention may also be performed in accordance with the method. Specifically, the magnesium oxide tablets of the present invention may be produced by combining the magnesium oxide granules, a binder, a disintegrant, etc. With the use of the magnesium oxide granules of the present invention, tableting problems including capping, laminating, sticking, picking, etc. are reduced.

The binder is not particularly limited, and examples thereof include carboxymethyl cellulose sodium, low substituted hydroxypropylcellulose, crystalline cellulose, starch (for example, corn starch), etc. The disintegrant is not particularly limited, and examples thereof include carboxymethyl cellulose calcium, carmellose, low substituted hydroxypropylcellulose, croscarmellose sodium, carmellose calcium, carboxy starch sodium, etc. The amount of the blended binder in the tablet is not particularly limited, and may be, for example, about 1 to about 10% by weight, preferably about 1 to about 8% by weight. Also, the amount of the blended disintegrant in the tablet is not particularly limited, and may be, for example, about 1 to about 10% by weight, preferably about 1 to about 5% by weight.

The tablet may further contain an excipient, a lubricant, etc. The excipient is not particularly limited, and examples thereof include lactose, sucrose, mannitol, corn starch, crystalline cellulose, etc. The lubricant is not particularly limited, and examples thereof include a sucrose fatty acid ester, polyethylene glycol, talc, stearic acid or a stearate (Na stearate, Mg stearate, or Ca stearate), etc.

Further, the tablet may contain one or more of additives, such as a plasticizer, a coating agent, an aggregation inhibitor, a solubilizer, a sweetener, an acidulant, a corrigent, a pH adjuster, a solubilizing aid, a colorant, or a flavor, if desired. Examples of the plasticizer include triethyl citrate, a glycerol fatty acid ester, polyethylene glycol, etc. Examples of the coating agent include ethyl cellulose, hydroxypropyl methylcellulose, etc. Examples of the aggregation inhibitor include talc, calcium stearate, etc. Examples of the solubilizer include a sucrose fatty acid ester, sorbitan monostearate, sodium lauryl sulfate, etc. Examples of the sweetener include aspartame, saccharin, dipotassium glycyrrhizate, stevia, etc. Examples of the acidulant (organic acid) include citric acid, malic acid, ascorbic acid, fumaric acid, etc. Examples of the corrigent include 1-menthol, sodium chloride, acesulfame potassium, sucralose, etc. Examples of the pH adjuster include a citrate, a phosphate, a carbonate, an acetate, etc. Examples of the solubilizing aid include cyclodextrin, arginine, lysine, trisaminomethane, etc. Examples of the colorant include yellow ferric oxide, red ferric oxide, sodium copper chlorophyllin, etc. Examples of the flavor include orange oil, lemon oil, mentha oil, eucalyptus oil, etc.

In view of the improvement in quality, the strength of the tablet of the present invention is preferably about 60 N to about 200 N.

In a preferred embodiment of the present invention, the tablet is preferably an orally disintegrating tablet. In this embodiment, the disintegration time of the tablet is not particularly limited, but for example, is usually about 1 to about 60 seconds, preferably about 5 to about 45 seconds, and more preferably about 5 to 20 seconds.

EXAMPLES

Hereinafter, the present invention will be illustrated in more detail by Experimental Examples and Examples, but the present invention is not limited thereto. Various modifications can be made within the technical idea of the present invention by those with ordinary skill in the art.

Method for Measuring CAA
(1) 100 mL of 0.4 N citric acid was adjusted to 30° C.
(2) One drop of phenolphthalein solution was added to the citric acid of the above (1).
(3) Magnesium oxide granules[(*)] were added to the solution resulting from the above (2), and the solution was stirred with a magnetic stirrer rotating at 550 rpm.
(4) The time (seconds) after the start of the stirring until the color of the tested solution changed from colorless to purplish red was determined as a CAA value.

[(*)] In the case where CAA40 was measured, 0.05 mol of the above magnesium oxide granules were added for the measurement. At the time when 0.02 mol of the magnesium oxide granules (40% of the total) are consumed for the reaction, the color of the tested solution changes from colorless to purplish red. In the case where CAA80 was measured, 0.025 mol of the above magnesium oxide granules were added for the measurement.

Method for Measuring Purity
The purity of the magnesium oxide granules was measured in accordance with the United States Pharmacopeia (USP).

Method for Measuring Bulk Density
Measurement was performed in accordance with the "Bulk Density Determination, Method 1" in the Japanese Pharmacopoeia.

Method for Measuring Pb Content and as Content
The contents were measured by the ICP-MS method. Specifically, the test sample (magnesium oxide granules) was dissolved in 7 N nitric acid. This sample solution was diluted with pure water, and then measurement was made using a coaxial nebulizer SPQ-9000 (made by Seiko Instruments). Separately, calibration curves were prepared using standard samples of Pb and As, and the Pb content and the As content in the magnesium oxide granules were calculated by the calibration curve method.

Method for Tableting and Method for Measuring Tablet Strength
(1) Magnesium oxide granules in an amount of 300 mg with 4 to 10% by weight of a binder added thereto were compacted at a pressure of 5 MPa using a tableting machine (HATA: HT-AP18 SS-II, No. 750) to give pellets having a diameter of 8 mm and a thickness of 4 mm. As the binder, starch was used.
(2) The tablet strength of the resulting pellets was measured using a tablet breaking-strength tester (Toyama Sangyo: TH303MP).

Reference Example 1

Production of Medium-Active Magnesium Oxide

Magnesium hydroxide (made by Konoshima Chemical Co., Ltd., Grade: #200) was calcined in an electric furnace at 900° C. for 2 hours to produce a medium-active magnesium oxide. The medium-active magnesium oxide obtained in this way had a BET specific surface area of 51 $m^2/g$.

Reference Example 2

Production of Low-Active Magnesium Oxide

Magnesium hydroxide (made by Konoshima Chemical Co., Ltd., Grade: #200) was calcined in an electric furnace at 1100° C. for 2 hours to produce a low-active magnesium oxide. The low-active magnesium oxide obtained in this way had a BET specific surface area of 3 $m^2/g$.

Example 1

The medium-active magnesium oxide having a BET specific surface area of 51 $m^2/g$ produced in Reference Example 1 (hereinafter referred to as medium-active MgO) and the low-active magnesium oxide having a BET specific surface area of 3 $m^2/g$ produced in Reference Example 2 (hereinafter referred to as low-active MgO) were mixed at a ratio of the medium-active MgO:the low-active MgO=80:20 (wt. %), and to the mixture, a roll pressure of 10 MPa was applied using a horizontal roller compactor made by Freund-Turbo Corp. Then, grinding was performed using a granulator (made by Nippon Granulator Co., Ltd., Model: GRN1031).

After the grinding, the granules were subjected to vibration sieving (20 mesh and 60 mesh), and granules remaining on the 20 mesh sieve and granules having passed through the 60 mesh were removed for the preparation of desired magnesium oxide granules.

Example 2

Magnesium oxide granules were produced in the same manner as in Example 1 except that the mixing ratio of the medium-active MgO and the low-active MgO was 60:40 (wt. %).

Example 3

Magnesium oxide granules were produced in the same manner as in Example 1 except that the mixing ratio of the medium-active MgO and the low-active MgO was 40:60 (wt. %).

Example 4

Magnesium oxide granules were produced in the same manner as in Example 1 except that the mixing ratio of the medium-active MgO and the low-active MgO was 20:80 (wt.).

Example 5

Magnesium oxide granules were produced in the same manner as in Example 1 except that the mixing ratio of the medium-active MgO and the low-active MgO was 10:90 (wt. %).

Comparative Example 1

Magnesium oxide granules were produced in the same manner as in Example 1 except that the medium-active MgO was used alone.

Comparative Example 2

Magnesium oxide granules were produced in the same manner as in Example 1 except that the low-active MgO was used alone.

Comparative Example 3

Magnesium oxide granules were produced in the same manner as in Example 1 except that a magnesium oxide having a BET specific surface area of 22 $m^2/g$ was used.

Table 1 shows the physical properties of the magnesium oxide granules, the tablet strength, and the presence or absence of tableting problems.

TABLE 1

|  | Medium-active MgO weight % | Low-active MgO weight % | BET $m^2/g$ | CAA40 s | CAA80 s | CAA80/40 — | Purity % | Bulk density g/L | Pb ppm | As ppm | Tablet strength N | Sticking, capping, chipping, etc. |
|---|---|---|---|---|---|---|---|---|---|---|---|---|
| Ex. 1 | 80 | 20 | 42 | 105 | 312 | 3.0 | 96.0 | 770 | <10 | <1 | 105 | No |
| Ex. 2 | 60 | 40 | 32 | 121 | 548 | 4.5 | 96.7 | 830 | <10 | <1 | 98 | No |
| Ex. 3 | 40 | 60 | 22 | 171 | 635 | 3.7 | 97.4 | 970 | <10 | <1 | 86 | No |
| Ex. 4 | 20 | 80 | 12 | 286 | 694 | 2.4 | 98.1 | 980 | <10 | <1 | 74 | No |
| Ex. 5 | 10 | 90 | 8 | 327 | 712 | 2.2 | 98.4 | 990 | <10 | <1 | 61 | No |
| Comp. Ex. 1 | 100 | 0 | 51 | 82 | 151 | 1.8 | 95.1 | 680 | <10 | <1 | 112 | Yes |
| Comp. Ex. 2 | 0 | 100 | 5 | 415 | 732 | 1.8 | 98.8 | 1070 | <10 | <1 | 46 | Yes |
| Comp. Ex. 3 | Medium low-active MgO | | 22 | 164 | 315 | 1.9 | 95.5 | 810 | <10 | <1 | 74 | Yes |

Ex.: Example
Comp. Ex.: Comparative Example

The magnesium oxide granules of Examples 1 to 4, which were embodiments of the present invention, did not cause tableting problems, such as sticking or capping, and the resulting tablets had sufficient strength.

INDUSTRIAL APPLICABILITY

With the use of the magnesium oxide granules of the present invention, tableting problems in the production of magnesium oxide tablets can be reduced, and quality defects resulting from insufficient strength of the tablets can also be reduced. As a result, the efficiency in the production of magnesium oxide tablets can be significantly improved. In addition, since the magnesium oxide granules of the present invention have less heavy metal content and high purity of magnesium oxide, the present invention can provide safe magnesium oxide granules that can be preferably used for pharmaceutical applications or as a food additive.

The invention claimed is:

1. Magnesium oxide granules for pharmaceutical applications or for use as a food additive having a BET specific surface area of 7 to 50 $m^2/g$ and CAA80/CAA40 of 2 to 7 and a bulk density of 700 to 1000 g/L.

2. The magnesium oxide granules according to claim 1 having a BET specific surface area of 10 to 45 $m^2/g$ and CAA80/CAA40 of 2.2 to 6.

3. The magnesium oxide granules according to claim 1 having a magnesium oxide purity (assay) of 96% or higher.

4. The magnesium oxide granules according to claim 1, wherein granules having a particle diameter of less than 150 μm account for 10% by weight or less of the total weight of the magnesium oxide granules.

5. The magnesium oxide granules according to claim 1 containing 20 ppm by weight or less of Pb and 4 ppm by weight or less of As relative to the total weight of the magnesium oxide granules.

6. The magnesium oxide granules according to claim 1, which is a mixture of a low-active magnesium oxide having CAA80 of 550 to 850 seconds and CAA40 of 250 to 550 seconds and a medium-active magnesium oxide having CAA80 of 100 to 300 seconds and CAA40 of 50 to 100 seconds.

7. The magnesium oxide granules according to claim 6, produced by mixing the low-active magnesium oxide and the medium-active magnesium oxide, applying pressure to the mixture, and grinding the mixture.

8. The magnesium oxide granules according to claim 6, wherein the low-active magnesium oxide has a BET specific surface area of 0.05 to 15 $m^2/g$ and the medium-active magnesium oxide has a BET specific surface area of 20 to 80 $m^2/g$.

9. The magnesium oxide granules according to claim 6, wherein the mixing ratio by wt. % of the medium-active magnesium oxide and the low-active magnesium oxide (the medium-active magnesium oxide:the low-active magnesium oxide) is 10:90 to 80:20.

10. A magnesium oxide tablet comprising the magnesium oxide granules according to claim 1.

11. A pharmaceutical composition comprising the magnesium oxide granules according to claim 1.

12. A food composition comprising the magnesium oxide granules according to claim 1.

13. The magnesium oxide granules according to claim 1 having CAA80/CAA40 of 2.2 to 7.

14. A method for producing the magnesium oxide granules according to claim 1, comprising the steps of mixing a medium-active magnesium oxide having CAA80 of 100 to 300 seconds and CAA40 of 50 to 100 seconds and a low-active magnesium oxide having CAA80 of 550 to 850 seconds and CAA40 of 250 to 550 seconds at a weight ratio of 10:90 to 80:20, applying pressure to the mixture, and grinding the mixture.

15. A method for producing a magnesium oxide tablet, comprising tableting the magnesium oxide granules according to claim 1.

* * * * *